United States Patent [19]
Deucher et al.

[11] Patent Number: 5,610,968
[45] Date of Patent: Mar. 11, 1997

[54] HIGH CAPACITY COOLING SYSTEM FOR CT GANTRY

[75] Inventors: Joseph S. Deucher, Lyndhurst; Anton Z. Zupancic, Kirtland; Nancy A. Udovic, Wickliffe, all of Ohio

[73] Assignee: Picker International, Inc., Highland Heights, Ohio

[21] Appl. No.: 406,131

[22] Filed: Mar. 17, 1995

[51] Int. Cl.$^6$ .................................................. H01J 35/10
[52] U.S. Cl. .......................... 378/199; 378/200; 378/2
[58] Field of Search .................... 378/199, 200, 378/4

[56] References Cited

U.S. PATENT DOCUMENTS

| | | | |
|---|---|---|---|
| 4,115,697 | 9/1978 | Hounsfield et al. | 250/445 T |
| 4,651,338 | 3/1987 | Hahn | 378/199 |
| 4,709,559 | 12/1987 | Dotzauer et al. | 62/499 |
| 4,866,743 | 9/1989 | Kroener | 378/4 |
| 4,969,167 | 11/1990 | Zupancic et al. | 378/19 |
| 5,012,505 | 4/1991 | Zupancic et al. | 378/130 |
| 5,299,249 | 3/1994 | Burke et al. | 378/15 |
| 5,313,512 | 3/1994 | Tanaka | 378/200 |

*Primary Examiner*—Don Wong
*Attorney, Agent, or Firm*—Fay, Sharpe, Beall, Fagan, Minnich & McKee

[57] ABSTRACT

A CT scanner includes a stationary gantry (C) having an examination region (12) centrally therein. A rotating frame or gantry (C) which is mounted for rotation about the examination region carries an x-ray tube assembly (B), a liquid-to-liquid heat exchanger (34), and a liquid-to-air heat exchanger (48) around a peripheral edge thereof. A first closed loop (30) carries a first cooling fluid, particularly oil, between a housing (22) which surrounds an x-ray tube (68) and the liquid-to-liquid heat exchanger to remove heat from the x-ray tube. A second closed loop (40) conveys a second cooling fluid, particularly water, between the liquid-to-liquid heat exchanger and the peripheral liquid-to-air heat exchanger. The second closed loop includes a reservoir (44) for storing a substantial volume of water such that a significant portion of the heat generated during an x-ray examination can be stored by the water in the reservoir. After the x-ray examination while the patient is being repositioned or removed, the water continues to be circulated to the liquid-to-air heat exchanger cooling the water from the reservoir.

20 Claims, 6 Drawing Sheets

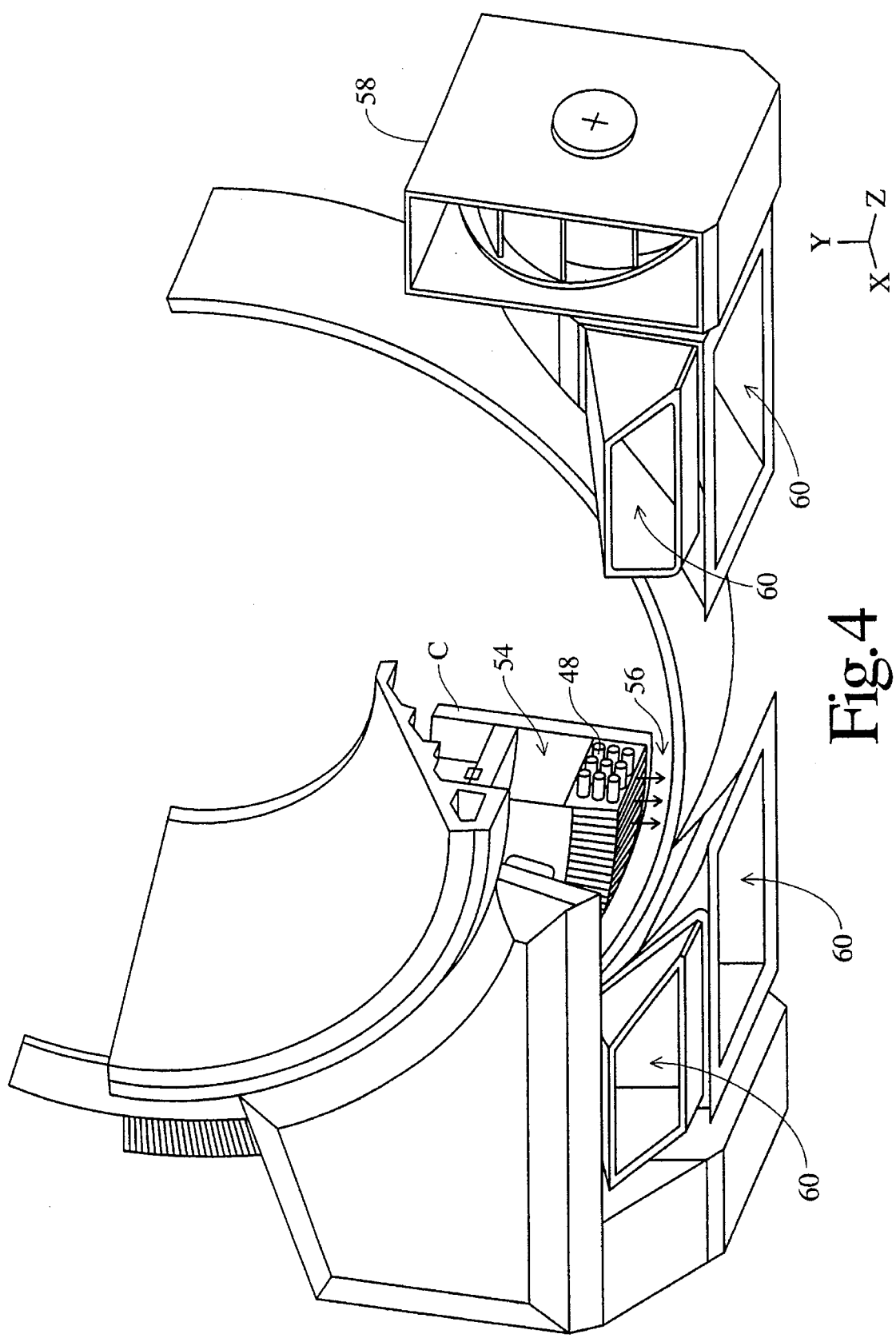

HIGH CAPACITY COOLING SYSTEM FOR CT GANTRY

BACKGROUND OF THE INVENTION

The present invention relates to the radiography art. It finds particular application in conjunction with computerized tomographic (CT) scanners and will be described with particular reference thereto. However, it is to be appreciated that the present invention may also find application in conjunction with other radiation treatment apparatus and imaging apparatus.

Heretofore, tomographic scanners have commonly included a floor-mounted frame assembly which remains stationary during a scan. An x-ray tube is mounted to a rotatable frame assembly which rotates around a patient receiving examination region during the scan. Radiation from the x-ray tube traverses the patient receiving region and impinges upon an array of radiation detectors. From the radiation data sampled by the detectors and the position of the x-ray tube during each sampling, a tomographic image of one or more slices through the patient is reconstructed.

An x-ray tube generates x-rays by directing a high energy electron bean against a tungsten target. One of the persistent problems in CT scanners and other radiographic apparatus is dissipating the waste heat created while generating x-rays. In higher powered x-ray tubes, the anode rotates so that the high energy electron beam only dwells a fraction of a second at a time on any point on the anode. The x-ray tube is jacketed with a lead lined housing. A cooling oil is circulated between a glass vacuum envelope of the x-ray tube and the lead-lined housing to remove waste heat.

In some scanners, the x-ray tube rotates in one direction during a scan and returns in the other direction for the next scan. Such scanners are normally limited to about 360° of rotation. The single rotation enables the hot cooling oil to be conveyed from the rotating frame by flexible hoses to a non-rotating heat exchanger. Accommodating the cooling oil-carrying hoses is a space consumptive handling problem. Limiting a scanner to about 360° of rotation makes it unable to perform many common diagnostic procedures.

In other CT scanners, the cooling oil is circulated to a radiator or other air-oil heat exchanger that is mounted on the rotating frame portion. This alleviates the hose handling problems and enables the x-ray tube to rotate a plurality of times, e.g., a continuous rotate scanner. However, accommodating the size and weight of the heat exchanger in the tight space constraints of the rotating frame is difficult. As the x-ray tube and rotating frame portion rotate, air passes through the heat exchanger cooling the oil. Limited space on the rotating gantry limits the surface area of the radiator, limiting cooling. In other CT scanners, hot oil or other hot fluid is conveyed to a fluid slip ring. The fluid slip ring is an annular structure that surrounds the patient bore. One part of the slip ring rotates with the rotating gantry and the other part is connected to the stationary gantry. An annular fluid passage is defined between the rotating and stationary slip ring halves. In one prior art design, the hot fluid circulated to a radiator immersed in the fluid in the slip ring. In another design, the hot fluid emptied into the fluid slip ring. In both designs, hot fluid from the slip ring was conveyed to a chiller. Surrounding the patient with a hot fluid carrying slip ring raises serious patient safety concerns. Leaking or failure of the slip ring seals could cause serious burns to the patient.

One of the limiting factors on the speed of a CT scan is the amount of x-rays produced by the x-ray tube. The tube must irradiate each detector for a sufficient duration that each detector receives the minimum total flux needed to reconstruct a good contrast image. Lower power tubes require the tube to dwell or focus longer on each detector. Larger, more powerful x-ray tubes supply the minimum flux more quickly, allowing the speed of x-ray tube rotation to be increased, hence the scan time decreased. However, as the x-ray tubes become more powerful, more heat is generated. More heat is also generated in continuous rotate scanners in which the tube remains "on" during several consecutive rotations for multi-slice imaging.

Larger x-ray tubes, such as seven inch anode x-ray tubes, generate so much heat that the prior art heat dissipation techniques are taxed. The limited air volume in the interior of a CT scanner limits the effectiveness of the rotating oil-air heat exchanger. Space constraints prevent larger heat exchangers from being accommodated on the rotating frame.

The present invention provides a new and improved cooling system which overcomes the above-referenced problems and others.

SUMMARY OF THE INVENTION

In accordance with the present invention, oil is circulated through a first fluid carrying passage peripherally around the rotating gantry of a CT scanner. The first fluid carrying passage is thermally connected to the x-ray tube and the circulating oil absorbs x-ray tube heat to cool the x-ray tube. Water is circulated through a second fluid carrying passage peripherally around the rotating gantry. A first heat exchanger thermally connects the first and second fluid carrying passages so that heat from the circulating oil is transferred to the circulating water. A second heat exchanger thermally connects the second fluid carrying passage and an air flow passage. Room air is circulated through the air flow passage and heat from the circulating water is transferred to the circulating air in the second heat exchanger. The heated air is then released into the room.

In accordance with a more limited aspect of the present invention, the x-ray tube is mounted on a rotatable frame that is continuously rotatable. An array of x-ray detectors are mounted to receive radiation from the x-ray tube that has traversed a patient examination region. An image reconstruction processor reconstructs an image representation from data received by the radiation detector array.

In accordance with another aspect of the present invention, an oil reservoir is connected with the first fluid carrying passage and an oil circulator circulates the oil through the first fluid carrying passage. A water reservoir is connected to the second fluid carrying passage and a water circulator circulates the water through the second fluid carrying passage.

In accordance with a yet more limited aspect of the present invention, at least one cold plate is connected to the second fluid carrying passage designed to liquid cool components of the scanner.

One advantage of the present invention is that it effectively cools large x-ray tubes and other large thermal loads.

Another advantage of the present invention is that it permits the x-ray tube and all associated oil conveying circuitry to be replaced as a unit to prevent cooling oil contamination.

Another advantage of the present invention is that it enables existing gantry configurations to carry a large heat exchanger that uses ambient room air to cool the circulating fluid. Additional refrigeration devices are not required.

Another advantage of the present invention is that it takes advantage of the normal duty cycle of a CT scanner x-ray tube.

Another advantage of the present invention is that a water coolant reservoir stores heat when the x-ray tube is on and the heat is dissipated between scans.

Another advantage of the present invention is that blowers run at a minimal speeds to minimize air movement noise.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 4 is an illustration in partial section of the second heat exchanger of the rotating gantry of FIG. 2 and a lower portion of the stationary gantry;

DETAILED DESCRIPTION OF THE PREFERRED EMBODIMENTS

Figure 1:
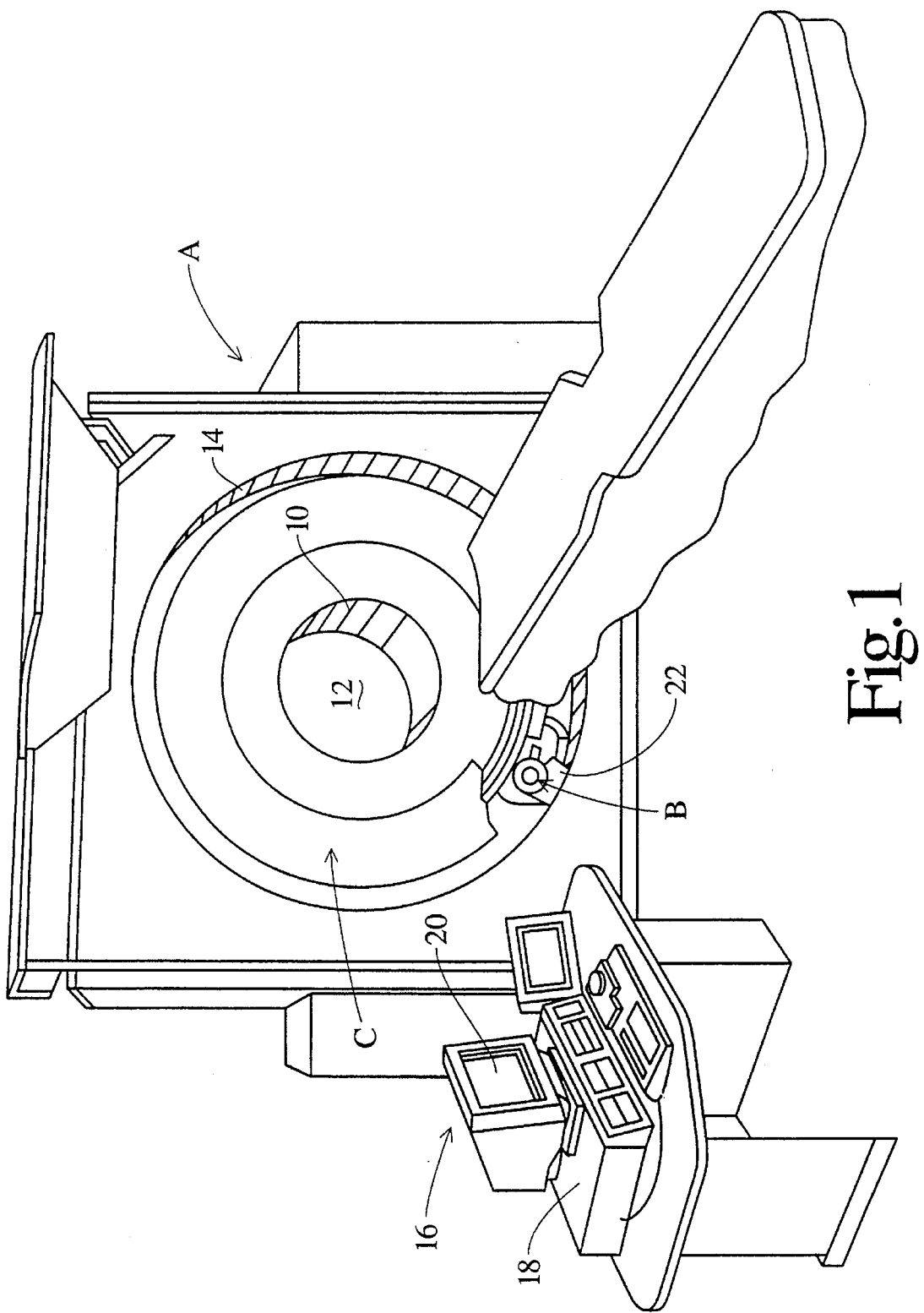
FIG. 1 is a diagrammatic illustration of a CT scanner in accordance with the present invention.

With reference to FIG. 1, a CT scanner includes a floor mounted or stationary gantry A whose position remains fixed during data collection. An x-ray tube B is rotatably mounted on a rotating gantry C. The stationary gantry A includes a cylinder 10 that defines a patient receiving examination region 12. An array of radiation detectors 14 are disposed concentrically around the patient receiving region. In the illustrated embodiment, the x-ray detectors are mounted on the stationary gantry portion such that an arc segment of the detectors receives radiation from the x-ray tube B which has traversed the examination region 12. Alternately, an arc segment of radiation detectors can be mounted to the rotating gantry C to rotate with the x-ray tube.

A control console 16 contains an image reconstruction processor 18 for reconstructing an image representation out of signals from the detector array 14. Preferably, the image reconstruction processor reconstructs a volumetric image representation from radiation attenuation data taken along a spiral path through the patient. A video monitor 20 converts selectable portions of the reconstructed volumetric image representation into a two-dimensional human-readable display. The console 16 also includes appropriate tape and disk recording devices for archiving image representations, performing image enhancements, selecting planes, 3D renderings, or color enhancements, and the like. Various scanner control functions such as initiating a scan, selecting among different types of scans, calibrating the system, and the like are also performed at the control console 16.

The x-ray tube B includes an oil filled housing 22 that has an x-ray permeable window directed toward the patient receiving region. An evacuated envelope is disposed within the housing holding a rotating anode, such as a 7 inch anode, and a cathode or other electron source. High voltages, on the order of 150 kV and higher applied between the rotating anode and the cathode, cause the generation of x-rays. The x-rays pass through an x-ray permeable window and across the patient receiving region 12. Appropriate x-ray collimators focus the radiation into one or more planar beams which span the examination region 12, as is conventional in the art. A shutter under control from the console 16 selectively gates the beam on and off to control patient dosage. Electrical power from the console is conveyed to electrical slip rings for transferring electrical power and control signals between the console and the x-ray tube, shutter and the like. A high voltage power supply 24 is mounted on the rotating gantry C for rotation with the x-ray tube. This permits relatively low voltage to be conveyed across the electrical slip ring and converted to high voltage on the rotating gantry.

Figure 2:
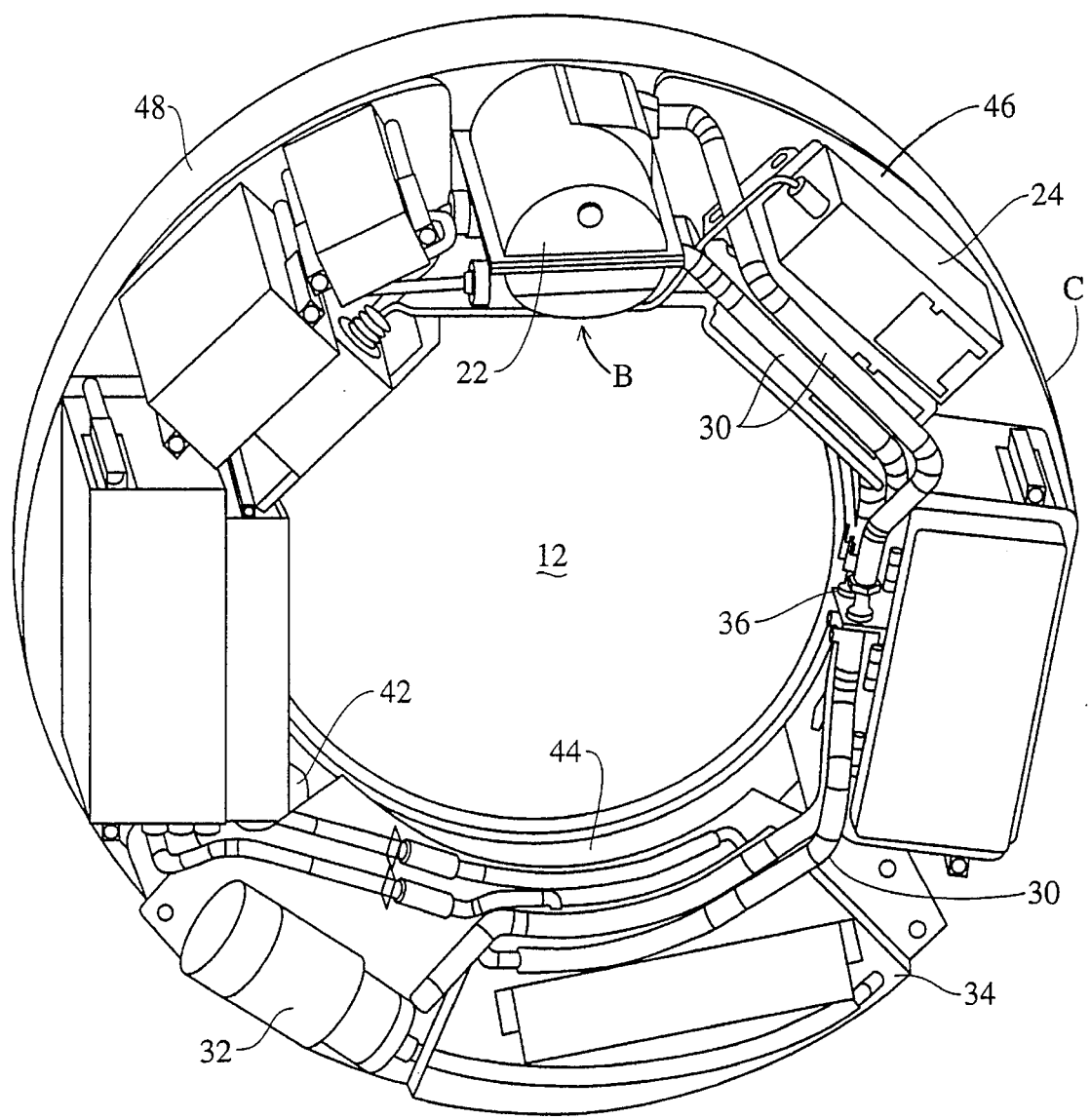
FIG. 2 is a perspective view of the rotating gantry of FIG. 1 with the front panel removed.
Figure 3:
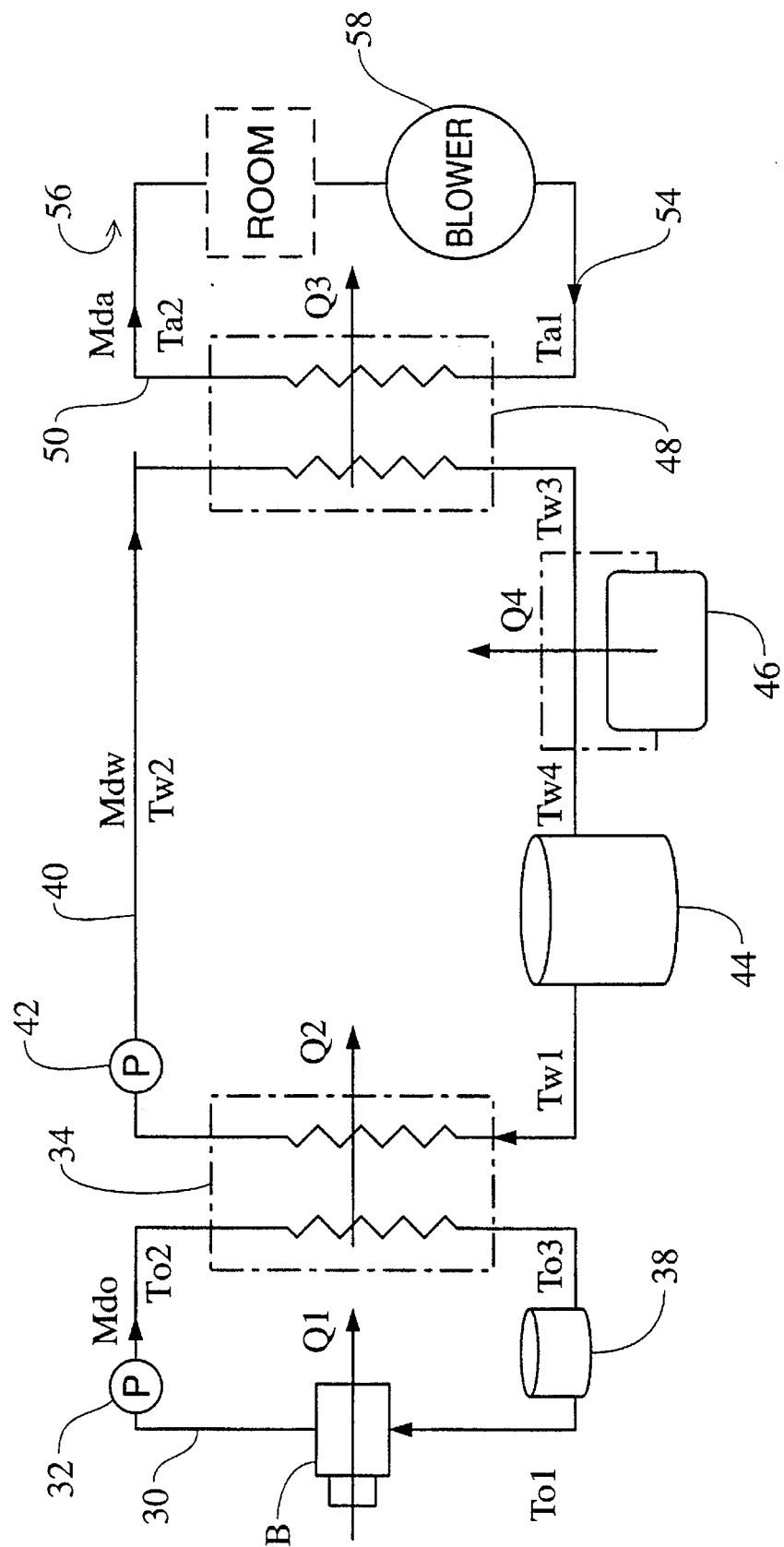
FIG. 3 is a schematic of the cooling system in accordance with the present invention.

With particular reference to FIGS. 2 and 3, a closed oil passage loop 30 is disposed on the rotating gantry C. The oil passage loop 30 is connected to the x-ray tube housing 22. An oil circulating pump 32 circulates oil through the oil passage loop 30 into and around the x-ray tube housing 22. As high voltages are applied between the rotating anode of the x-ray tube and the cathode, x-rays are generated along with a substantial amount of heat Q1. The circulating oil absorbs the heat generated from the x-ray tube cooling the x-ray tube. The heated oil then circulates through an oil-water or first heat exchanger 34 which has an effective steady-state counterflow heat capacity UA1. The first heat exchanger 34 includes a plurality of annular loops of tubing that define passages through which the heated oil is circulated. The tubes are interconnected by webs which increase the heat transfer surface area. The oil passage loop 30 has a line disconnect mechanism 36 which allows the x-ray tube B to be removed from the loop for maintenance or replacement. An oil reservoir 38 is connected to the oil passage loop to maintain an oil supply. Alternatively, other working fluids or mediums may be used in place of Oil.

The first heat exchanger 34 thermally connects the oil passage loop with a water passage loop 40. The water passage loop is annularly disposed around the gantry forming a closed loop. A water circulating pump 42 circulates water through the water passage. As the water circulates through the first heat exchanger, heat from the heated oil in the oil passage loop is transferred to the circulating water. In this manner, the heated oil is cooled. A 10 gallon water reservoir 44 is connected to the water passage to maintain a supply of water and provide a thermal reservoir. The water reservoir 44 functions as a heat sink by increasing the thermal mass of the water passage. The water reservoir is positioned opposite the x-ray tube B on the gantry and additionally functions as a counter-weight. Other working fluids or mediums may also be used in place of water. Cold plates 46 are connected to the water passage to cool the high voltage generator 24 or other rotating gantry mounted electronic or heat sensitive components. The water from the water pump 42 is pumped through a water-air or second heat exchanger 48.

With reference to FIGS. 3 and 4, an air flow passage 50 is defined by stationary ducts disposed around the gantry. The air flow passage is an open-ended loop so that air is drawn from and released into the surrounding room. The second heat exchanger 48 thermally connects the air flow passage and the water passage loop. In the preferred embodiment, the second heat exchanger 48 is a large diameter circular radiator and has an effective steady-state counter-flow heat capacity UA2. The water-air heat exchanger includes a series of radial vanes that surround the rotating gantry C. As the rotating gantry rotates, the vanes function as a squirrel cage blower to pump cool air from a plenum 54 through the vanes and discharging hot air to an annular surrounding region 56 of the air passage 50. Variable speed blowers 58 are mounted on the stationary gantry to draw cool ambient room air through the input ducts 60 to provide a positive air flow into the plenum 54. In this manner, heat from the circulating water is transferred to the air, thus cooling the water. Hot air from annular region 56 is discharged into the room or can be connected to ceiling ducts which remove the heated air from the room. It is to be appreciated that excess heat in the room air can be removed in a number of ways as known by those of ordinary skill in the art.

Sensors monitor temperature, pressure, and flow of the cooling system. The sensor measurements are inputted to a thermal controller which monitors system status and performance. The thermal controller controls air circulating speed, dampeners, blower speeds, air supply, and exhaust ducts, and produces signals indicating when maintenance is needed. Furthermore, because the oil and water passages are closed loops, volume expansion devices, preferably accumulators (not shown), are connected to the passages to maintain stability.

With further reference to FIG. 3, the definitions of the cooling system variables are:

$T_{o1}$: Temp of oil entering x-ray tube B;

$T_{o2}$: Temp of oil exiting x-ray tube B;

$T_{w1}$: Temp of water entering first heat exchanger 34;

$T_{w2}$: Temp of water exiting first heat exchanger $T_{a1}$: Temp of air entering second heat exchanger 48;

$T_{a2}$: Temp of air exiting second heat exchanger 48;

$Q_1$: Heat flow from the x-ray tube B;

$Q_2$: Heat flow across first heat exchanger $Q_3$: Heat flow across second heat exchanger 48;

$Q_4$: Heat flow across the generator $M_{do}$: Oil flow rate;

$M_{dw}$: Water flow rate;

$M_{da}$: Air flow rate;

UA1: First heat exchanger capacity; and,

UA2: Second heat exchanger capacity.

The cooling system is designed to move heat $Q_1$ created by the x-ray tube B to the air at $Q_3$. The rate at which the heat is removed from this system is dictated by:

(1) overall temperature differential, found by the difference between the hot oil temperature $T_{o2}$ leaving the x-ray tube and the cold air temperature $T_{a2}$ entering the second heat exchanger 48;

(2) heat exchanger capacities; and, (3) mass flow rates of the oil, water, and air represented by $M_{do}$, $M_{dw}$, and $M_{da}$.

Items (2) and (3) above are limited by packaging restraints. Item (1) is limited by the type of flow control within the tube housings of the fluids.

Two flow control embodiments effect the temperature differential of the system. The first is a flow through embodiment shown in FIGS. 5A and 5B, and the second is a counterflow embodiment shown in FIGS. 6A–6B.

Figure 5A:
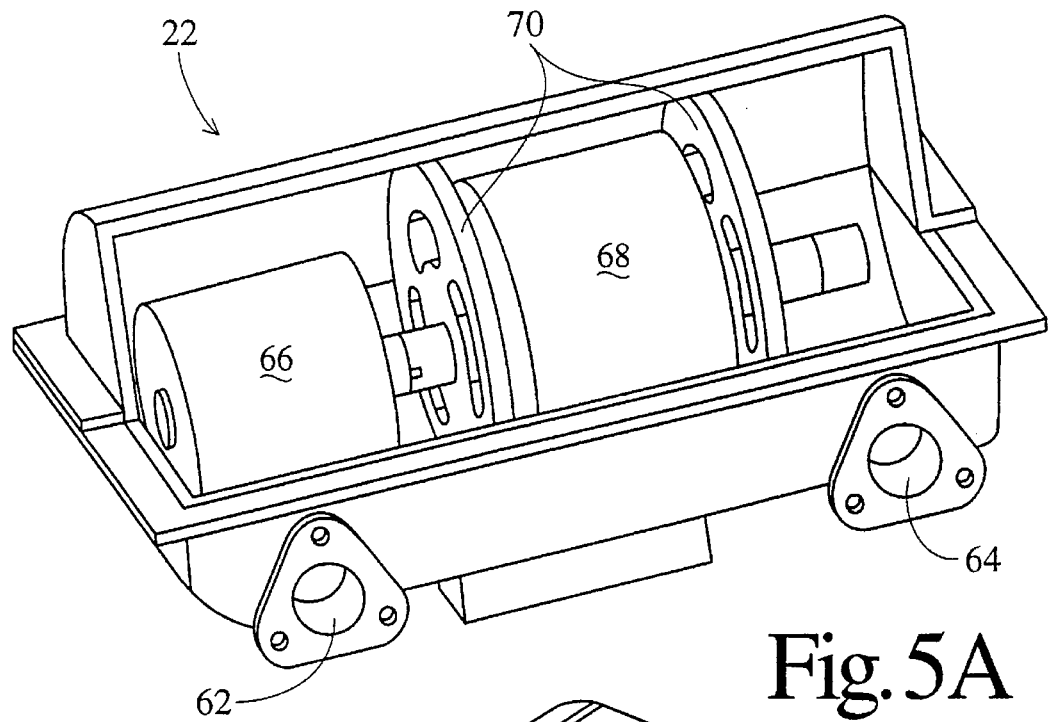
FIG. 5A is a perspective view in partial section of one embodiment of the x-ray tube.

With reference to FIG. 5A, a cutaway view of housing 22 of x-ray tube B is shown for the flow through embodiment. The x-ray tube housing 22 has an oil inlet port 62 and an oil outlet port 64 which connect to the oil passage loop 30. A motor 66 rotates an x-ray tube evacuated envelope 68 to which the anode is attached. The surface of the anode and housing are channeled or vaned to urge oil flow from the inlet port 62 through apertures in baffles 70 over the surface of the evacuated envelope 70 to the outlet port 64.

Figure 5B:
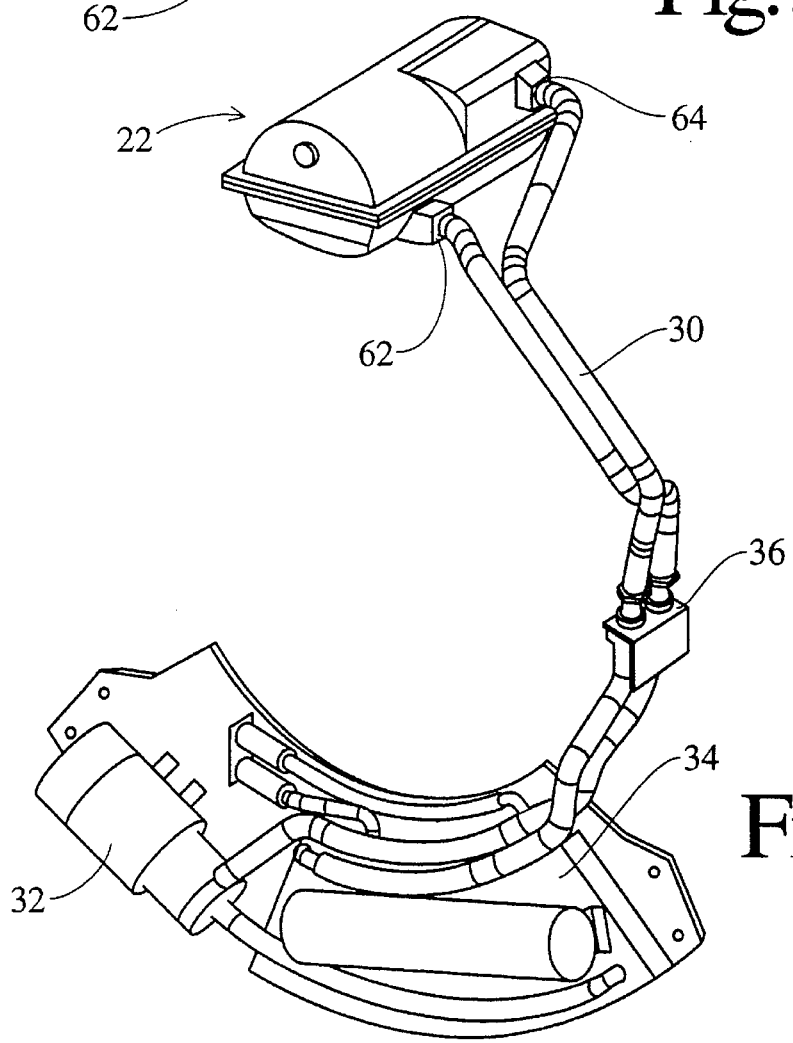
FIG. 5B illustrates an oil cooling arrangement in accordance with the embodiment of FIG. 5A of the x-ray tube.

With reference to FIG. 5B, an oil cooling arrangement for the flow through embodiment is shown. This arrangement corresponds to the embodiment shown in FIG. 2. In the flow through embodiment, the temperature of oil exiting the x-ray tube at outlet 64 is limited by the thermal sensitivity of components located within the x-ray tube housing 22, in the preferred embodiment about 65° C.

The cooling system shown in FIG. 2 is sized to match the flow through embodiments requirements. By numerical simulation, the steady-state maximum oil temperature at the end of a 160 second 57 kW, 33% duty cycle run is 75° C. This temperature is determined based on a 24° C. inlet air temperature $T_{a1}$ to the second heat exchanger 48. Since the maximum oil temperature of $T_{o2}$ reduces proportionally to the inlet air temperature $T_{a1}$, a maximum oil temperature of 65° C. will result if 14° C. inlet air is provided.

Figure 6A:
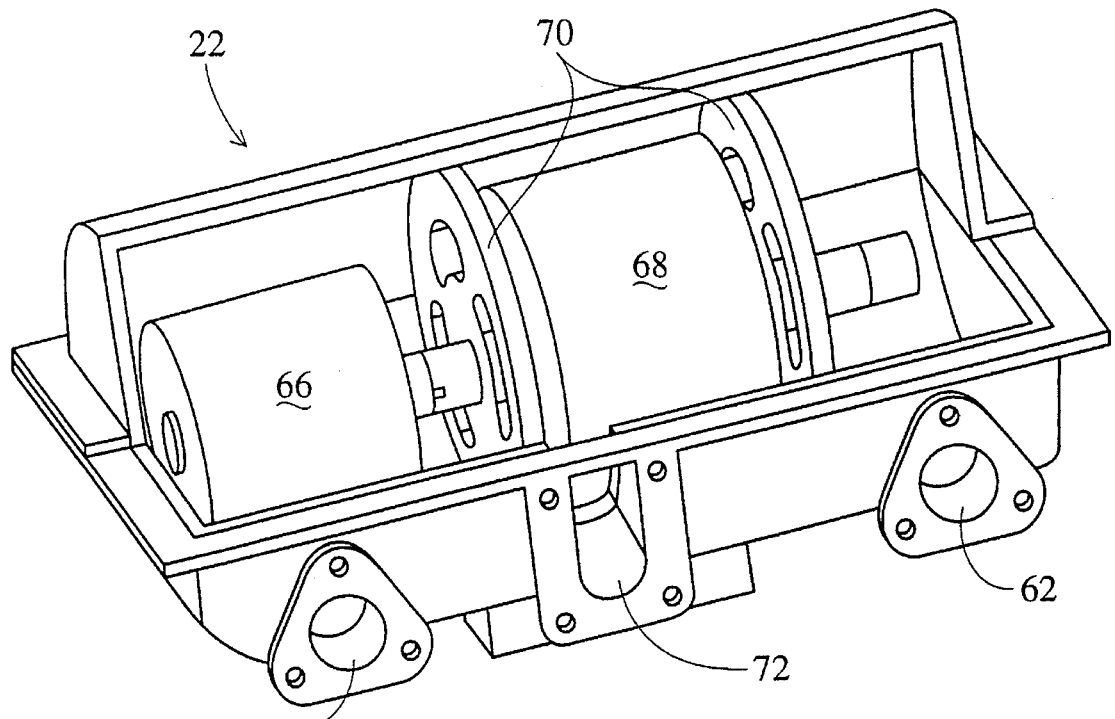
FIG. 6A is a perspective view in partial section of an alternative embodiment of the x-ray tube housing; and, FIG. 6B is a perspective view of an oil cooling system in accordance with the alternative embodiment of FIG. 6A.

With reference to FIG. 6A, a cutaway of the x-ray tube housing 22 is shown for the counterflow embodiment. A motor 66 and stationary baffles 70 are mounted on either side of the evacuated envelope 68 of x-ray tube B within the housing 22. The housing 22 has two oil inlet ports 62 and an oil discharge port 72. The anode, on the motor side of the evacuated envelope and in alignment with the discharge port has radial vanes that form a centrifugal pump to pump oil out of the discharge port. The baffles 70 have apertures that are seized such that most of the oil flows over the motor 66 and only a smaller component flows over the evacuated envelope 68.

Figure 6B:
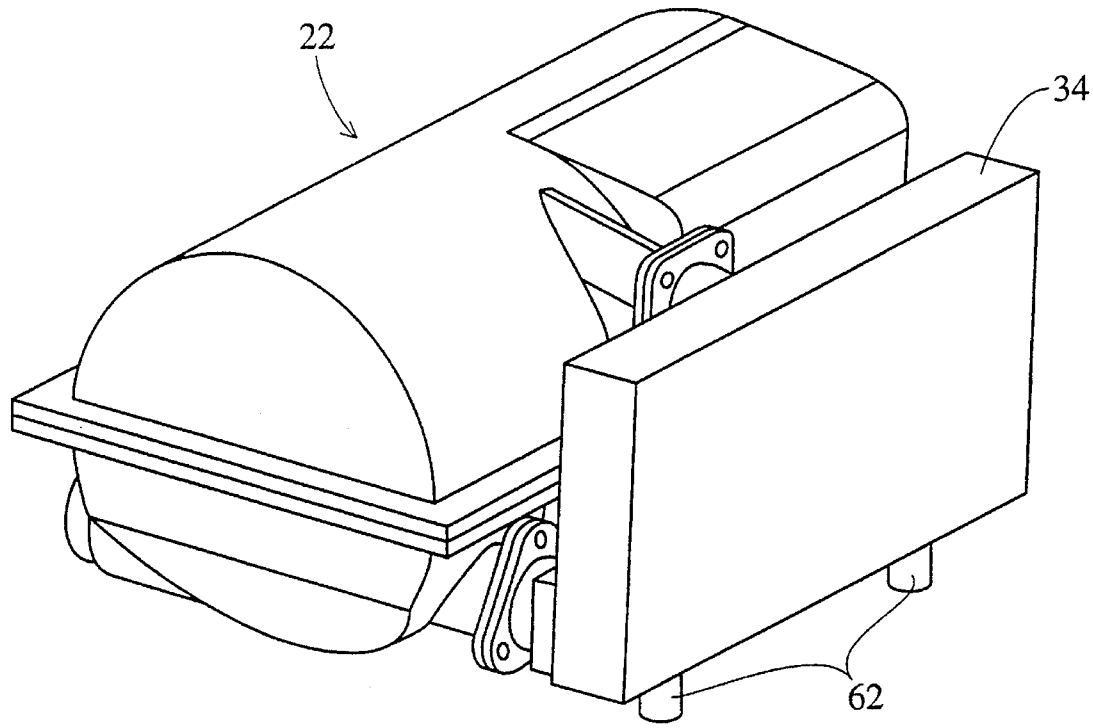

With reference to FIG. 6B, an oil cooling arrangement is shown for the counterflow embodiment. In this embodiment, the primary or oil-water heat exchanger 34 is directly connected with the x-ray tube housing 22. With further reference to FIGS. 6A and 3, the counterflow embodiment keeps the hot oil separate from the heat sensitive components. This allows the oil temperature of inlet oil temperature $T_{o1}$ entering inlet ports 62 to be higher, e.g., 65° C. and the temperature of the oil $T_{o2}$ exiting port 72 to be around 100° C. With a larger temperature differential heat exchanger, components and pump sizes are greatly downsized. Reduction of flow rates reduces the overall size of the cooling system as well as reducing noise. Further reduction of the first heat exchanger capacity results in a reduction in heat exchanger volume as well as a cost savings. Downsizing of the first heat exchanger further eliminates quick disconnects in the oil loop which aid in the serviceability of the x-ray tube.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A CT scanner comprising:

a patient receiving region defined within a stationary gantry;

an x-ray tube mounted on a rotating frame for rotation about the patient receiving region, the x-ray tube having an x-ray window through which x-rays are transmitted across the patient receiving region;

a radiation detector for detecting x-rays which have traversed the patient receiving region and generating signals indicative of the radiation detected;

an image reconstruction processor for reconstructing an image representation from the signals generated by the radiation detector;

a first heat exchanger mounted on the rotating frame for transferring heat from a first cooling fluid to a second cooling fluid;

a first closed cooling fluid loop for conveying the first cooling fluid in a closed loop between the x-ray tube and the first heat exchanger;

a second heat exchanger mounted around a periphery of the rotating frame for transferring heat from the second cooling fluid to air;

a second cooling fluid loop mounted on the rotating frame for conveying the second cooling fluid in a closed loop between the first and second heat exchangers.

2. The CT scanner as set forth in claim 1 further including:

a thermal reservoir for temporarily storing heat from the x-ray tube.

3. The CT scanner as set forth in claim 2 wherein the thermal reservoir includes a reservoir in fluid communication with the second cooling fluid loop for storing hot second cooling fluid:

a second cooling fluid pump for circulating the second cooling fluid from the reservoir to the second heat exchanger for dissipating the stored heat.

4. The CT scanner as set forth in claim 3 wherein the reservoir is disposed on the rotating frame opposite the x-ray tube such that the reservoir serves as a counterweight to the x-ray tube.

5. The CT scanner as set forth in claim 1 further including:

an annular plenum formed between the rotating frame and the stationary gantry along the second heat exchanger; and, an air circulator mounted on the stationary gantry for pumping air into the plenum.

6. The CT scanner as set forth in claim 5 wherein the air circulator is variable speed and further including:

a thermal controller which monitors a temperature of the first cooling fluid and controls a speed of the air circulator in accordance with the monitored temperature.

7. The CT scanner as set forth in claim 1 further including:

a thermal controller mounter on the stationary gantry for monitoring and controlling temperature, pressure, and flow of the first and second cooling fluids and the air.

8. The CT scanner as set forth in claim 1 wherein the second heat exchanger includes a multiplicity of radially disposed vanes such that rotation of the rotating frame urges the air to flow between the vanes from a central portion of the rotating frame toward a periphery of the rotating frame.

9. The CT scanner as set forth in claim 8 wherein the second heat exhanger extends circumferentailly around the rotating frame and further including:

an annular plenum defined between the rotating frames, the stationary gantry, and an inner circumference of the second heat exchanger;

an air pump for circulating air through the plenum and radially through the second heat exchanger vanes.

10. The CT scanner as set forth in claim 1 wherein the second cooling fluid loop includes a plate through which the second cooling fluid is circulated, electronic components being mounted on the plate such that heat from the electronic components is removed through the plate to the second cooling fluid.

11. The CT scanner as set forth in claim 1 wherein the x-ray tube includes a generally cylindrical housing with an anode at one end thereof, the anode having radial vanes such that as the x-ray tube and anode are rotated, the vanes function as a centrifugal pump, the x-ray tube anode and envelope being mounted in a housing which has inlets adjacent opposite ends thereof for receiving the first cooling fluid from the first cooling fluid loop and an outlet port disposed adjacent the anode vanes such that the anode vanes pump the first cooling fluid through the outlet port into the first cooling fluid loop.

12. The CT scanner as set forth in claim 11 wherein the first heat exchanger is mounted directly to the x-ray tube housing and is connected to the inlet and outlet ports of the x,ray tube housing.

13. In an x-ray apparatus having a subject receiving region defined within a stationary gantry, an x-ray tube mounted within a housing with cooling passages therebetween for passage of a first cooling liquid, the x-ray tube housing being mounted on a rotating frame for rotation about the subject receiving region, the x-ray tube and housing having x-ray transparent windows through which x-rays are transmitted across the subject receiving region when the x-ray tube is activated, the improvement comprising:

a first closed cooling liquid loop for conveying the first cooling liquid between the x-ray tube housing and a liquid-to-liquid heat exchanger for removing heat generated when the x-ray tube is activated;

a second closed cooling liquid loop for conveying a second cooling liquid between the liquid-to-liquid heat exchanger and a liquid-to-air heat exchanger, the second closed cooling liquid loop including:

a fluid reservoir for storing the heat generated when the x-ray tube is activated, a tubing system interconnecting the liquid-to-liquid heat exchanger with the reservoir, the reservoir with the liquid-to-air heat exchanger, and the liquid-to-air heat exchanger to the liquid-to-liquid heat exchanger, and a pump for continuing to circulate the second liquid from the liquid-to-liquid heat exchanger to the reservoir, from the reservoir through the liquid-to-air heat exchanger, and the liquid-to-liquid heat exchanger when the x-ray tube is off such that the heat stored in the reservoir is dissipated.

14. In an x-ray apparatus having a subject receiving region defined within a stationary gantry an x-ray tube mounted within a housing with cooling passages therebetween for passage of a first cooling liquid, the x-ray tube housing being mounted on a rotating frame for rotation about the subject receiving region, the x-ray tube and housing having an x-ray transparent window through which x-rays are transmitted across the subject receiving region, the improvement comprising:

a first closed cooling liquid loop for conveying the first cooling liquid between the x-ray tube housing and a liquid-to-liquid heat exchanger;

a second closed cooling liquid loop for conveying a second cooling liquid between the liquid-to-liquid heat exchanger and a liquid-to-air heat exchanger, the liquid-to-air heat exchanger including a multiplicity of radially disposed fins disposed circumferentially around a periphery of the rotating frame; and at least one of the first and second closed cooling liquid loops storing heat when the x-ray tube is activated and dissipating heat through the liquid-to-air heat exchanger when the x-ray tube is off.

15. In an x-ray apparatus having a subject receiving region defined within a stationary gantry, an x-ray tube mounted within a housing with cooling passages therebetween for passage of a first cooling fluid, the x-ray tube housing being mounted on a rotating frame for rotation about the subject receiving region, the x-ray tube and housing having x-ray transparent windows through which x-rays are transmitted across the subject receiving region, the improvement comprising:

a motor mounted within the x-ray tube housing for rotating the x-ray tube;

the x-ray tube having vanes for pumping the first cooling fluid;

the housing having at least one inlet port disposed adjacent an end thereof and an outlet port disposed adjacent the vanes of the x-ray tube;

a first closed cooling fluid loop connected with the housing inlet and outlet ports and a first heat exchanger for circulating a first cooling fluid; and a second closed cooling fluid loop for circulating a second cooling liquid between the first heat exchanger and a second heat exchanger for discharging heat from the second cooling fluid into air.

16. In the x-ray apparatus as set forth in claim 15, the improvement further comprising:

the liquid-to-liquid heat exchanger being mounted to the housing in direct fluid connection with the inlet and outlet ports.

17. In an x-ray diagnostic method in which an x-ray tube which is rotating around an examination region and is intermittently gated on to generate x-rays which are transmitted across the subject receiving region irradiating a subject therein and in which the x-ray tube is cooled by circulating a first cooling liquid thereover, the improvement comprising:

circulating the first cooling liquid from the x-ray tube to a liquid-to-liquid heat exchanger; and circulating a second cooling liquid between the liquid-to-liquid heat exchanger and a liquid-to-air heat exchanger, the liquid-to-air heat exchanger including a multiplicity of radially oriented fins disposed around a circumference of the rotating frame such that as the rotating frame rotates, the vanes of the liquid-to-air heat exchanger function as a centrifugal pump to urge cooling air radially therebetween.

18. In an x-ray diagnostic method in which an x-ray tube which is rotating around an examination region and is intermittently gated on to generate x-rays which are transmitted across the subject receiving region irradiating a subject therein and in which the x-ray tube is cooled by circulating a first cooling liquid there over, the improvement comprising:

circulating the first cooling liquid along a first cooling route from the x-ray tube to a liquid-to-liquid heat exchanger;

circulating a second cooling liquid along a second cooling route between the liquid-to-liquid heat exchanger and a liquid-to-air heat exchanger; and providing a reservoir storing the second cooling liquid along the second cooling route between the liquid-to-liquid heat exchanger and the liquid-to-air heat exchanger, the reservoir having a fluid capacity such that the second cooling liquid in the reservoir stores at least half the thermal energy generated by the x-ray tube during an examination and continuing to circulate the second cooling fluid from the reservoir through the liquid-to-air heat exchanger after the examination such that thermal energy stored in the reservoir is dissipated through the liquid-to-air heat exchanger between x-ray tube operations.

19. A method of diagnostic imaging comprising:

rotating a rotatable frame which carries an x-ray tube disposed within a housing, the x-ray tube having vanes disposed thereon, a liquid-to-liquid heat exchanger, and a liquid-to-air heat exchanger mounted around a periphery thereof, the liquid-to-air heat exchanger having generally radially oriented vanes;

rotating the x-ray tube within the housing such that the x-ray tube vanes pump a first liquid between the x-ray tube and the x-ray tube housing to remove heat from the x-ray tube, to the liquid-to-liquid heat exchanger to transfer the heat to a second liquid, and back to the x-ray tube housing;

circulating the second liquid between the liquid-to-liquid heat exchanger and the liquid-to-air heat exchanger to dissipate the heat to the ambient air;

as the frame rotates, circulating the ambient air through the vanes of the liquid-to-air heat exchanger;

intermittently actuating the x-ray tube to generate x-rays and pass a beam of x-rays through the examination region;

detecting x-rays transmitted across the examination region and converting intensities of detected x-rays into electronic data;

transforming the collected data into electronic image representations.

20. A method of diagnostic imaging comprising:

rotating a rotatable frame which carries an x-ray tube disposed within a housing, a liquid-to-liquid heat exchanger, and a liquid-to-air heat exchanger mounted around a periphery thereof, the liquid-to-air heat exchanger having generally radially oriented vanes;

circulating a first liquid between the X-ray tube housing and the liquid-to-liquid heat exchanger;

circulating a second liquid between the liquid-to-liquid heat exchanger and the liquid-to-air heat exchanger;

as the frame rotates, circulating air through the vanes of the liquid-to-air heat exchanger;

gating the x-ray tube on intermittently for preselected durations to generate X-rays and pass a beam of x-rays through the examination region;

collecting heat generated during the preselected duration in which the x-ray tube is on in a reservoir of the second cooling fluid disposed between the liquid-to-liquid heat exchanger and the liquid-to-air heat exchanger;

after the durations in which the x-ray tube is gated on, continuing to rotate the rotating frame and continuing to circulate at least the second cooling fluid such that the heat in the reservoir is dissipated to the air;

detecting X-rays transmitted across the examination region and converting intensities of detected x-rays into electronic data;

transforming the collected data into electronic image representations.

* * * * *